(12) United States Patent
Song

(10) Patent No.: US 7,829,347 B2
(45) Date of Patent: *Nov. 9, 2010

(54) DIAGNOSTIC TEST KITS WITH IMPROVED DETECTION ACCURACY

(75) Inventor: Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 488 days.

This patent is subject to a terminal disclaimer.

(21) Appl. No.: 11/217,112

(22) Filed: Aug. 31, 2005

(65) Prior Publication Data

US 2007/0048807 A1    Mar. 1, 2007

(51) Int. Cl.
*G01N 33/53* (2006.01)

(52) U.S. Cl. .................. 436/518; 436/514; 436/512; 436/513; 436/531; 436/526; 436/533; 436/538; 436/806; 436/824; 435/2; 435/5; 435/287.2; 435/287.9; 435/803; 435/805; 435/970; 422/56; 422/58; 422/61

(58) Field of Classification Search .................. 435/7.1, 435/7.92, 7.2, 2, 5, 7.21, 7.32, 239, 803, 435/805, 287.2, 287.9, 970; 436/512, 513, 436/518, 514, 531, 526, 533, 538, 806, 824; 422/56, 58, 61

See application file for complete search history.

(56) References Cited

U.S. PATENT DOCUMENTS 4,168,146 A    9/1979    Grubb et al.
4,235,601 A    11/1980   Deutsch et al.
4,366,241 A    12/1982   Tom et al.

(Continued)

FOREIGN PATENT DOCUMENTS

AU    7 59407 B2    2/2000

(Continued)

OTHER PUBLICATIONS

U.S. Appl. No. 11/094,498, filed Mar. 30, 2005, Song et al., Diagnostic Test Kits Employing an Internal Calibration System.
U.S. Appl. No. 11/119,262, filed Apr. 29, 2005, Song et al., Assay Devices Having Detection Capabilities Within the Hook Effect Region.

(Continued)

*Primary Examiner*—Bao-Thuy L Nguyen
(74) *Attorney, Agent, or Firm*—Dority & Manning, P.A.

(57) ABSTRACT

A diagnostic test kit that provides an integrated system for accurately detecting a test analyte over a broad range of possible concentrations is provided. One feature of the integrated system is that it is capable of indicating whether an analyte is within the "hook effect" region. Based on this indication, a technique may be selected for correlating a measured signal intensity to an analyte concentration or range of concentrations. For example, when it is determined that the test sample falls outside the "hook effect" region, the analyte concentration may be determined using one portion of a dose response curve. On the other hand, when it is determined that the test sample falls within the "hook effect" concentration, the analyte concentration may be determined using another portion of the dose response curve. Alternatively, the sample may simply be diluted for re-performing the assay. Regardless of whether the test sample is within or outside of the "hook effect" concentration, another feature of the integrated detection system of the present invention is that it is internally calibrated to provide a more accurate quantitative or semi-quantitative result to a user.

17 Claims, 6 Drawing Sheets

U.S. PATENT DOCUMENTS

| | | | |
|---|---|---|---|
| 4,385,126 A | 5/1983 | Chen et al. |
| 4,435,504 A | 3/1984 | Zuk et al. |
| 4,442,204 A | 4/1984 | Greenquist et al. |
| 4,540,659 A | 9/1985 | Litman et al. |
| 4,614,723 A | 9/1986 | Schmidt et al. |
| 4,742,011 A | 5/1988 | Blake et al. |
| 4,743,542 A | 5/1988 | Graham, Jr. et al. |
| 4,743,560 A | 5/1988 | Campbell et al. |
| 4,806,312 A | 2/1989 | Greenquist |
| 4,835,099 A | 5/1989 | Mize et al. |
| 4,843,000 A | 6/1989 | Litman et al. |
| 4,889,816 A | 12/1989 | Davis et al. |
| 4,904,583 A | 2/1990 | Mapes et al. |
| 4,920,046 A | 4/1990 | McFarland et al. |
| 4,954,435 A | 9/1990 | Krauth |
| 4,956,302 A | 9/1990 | Gordon et al. |
| 4,978,625 A | 12/1990 | Wagner et al. |
| 4,980,298 A | 12/1990 | Blake et al. |
| 5,028,535 A | 7/1991 | Buechler et al. |
| 5,073,340 A | 12/1991 | Covington et al. |
| 5,075,077 A | 12/1991 | Durley, III et al. |
| 5,075,078 A | 12/1991 | Osikowicz et al. |
| 5,089,391 A | 2/1992 | Buechler et al. |
| 5,120,643 A | 6/1992 | Ching et al. |
| 5,149,622 A | 9/1992 | Brown et al. |
| 5,185,127 A | 2/1993 | Vonk |
| 5,208,143 A | 5/1993 | Henderson et al. |
| 5,208,535 A | 5/1993 | Nakayama et al. |
| 5,252,459 A | 10/1993 | Tarcha et al. |
| 5,275,785 A | 1/1994 | May et al. |
| 5,387,503 A * | 2/1995 | Selmer et al. ............... 435/5 |
| 5,395,754 A | 3/1995 | Lambotte et al. |
| 5,428,690 A | 6/1995 | Bacus et al. |
| 5,464,741 A | 11/1995 | Hendrix |
| 5,518,883 A | 5/1996 | Soini |
| 5,573,909 A | 11/1996 | Singer et al. |
| 5,573,919 A | 11/1996 | Kearns et al. |
| 5,585,279 A | 12/1996 | Davidson |
| 5,591,581 A | 1/1997 | Massey et al. |
| 5,591,645 A | 1/1997 | Rosenstein |
| 5,602,040 A * | 2/1997 | May et al. ............... 436/514 |
| 5,610,077 A | 3/1997 | Davis et al. |
| 5,622,871 A | 4/1997 | May et al. |
| 5,637,509 A | 6/1997 | Hemilä et al. |
| 5,656,503 A | 8/1997 | May et al. |
| 5,670,381 A | 9/1997 | Jou et al. |
| 5,714,389 A | 2/1998 | Charlton et al. |
| 5,731,147 A | 3/1998 | Bard et al. |
| 5,788,863 A | 8/1998 | Milunic |
| 5,798,273 A | 8/1998 | Shuler et al. |
| 5,856,203 A | 1/1999 | Robinson et al. |
| 5,922,537 A | 7/1999 | Ewart et al. |
| 5,945,281 A | 8/1999 | Prabhu |
| 5,968,839 A | 10/1999 | Blatt et al. |
| 5,989,924 A | 11/1999 | Root et al. |
| 5,989,926 A | 11/1999 | Badley et al. |
| 5,998,221 A | 12/1999 | Malick et al. |
| 6,004,530 A | 12/1999 | Sagner et al. |
| 6,027,944 A | 2/2000 | Robinson et al. |
| 6,030,840 A | 2/2000 | Mullinax et al. |
| 6,057,165 A | 5/2000 | Mansour |
| 6,077,669 A | 6/2000 | Little et al. |
| 6,103,536 A | 8/2000 | Geisberg |
| 6,121,008 A | 9/2000 | Fitzpatrick et al. |
| 6,130,100 A | 10/2000 | Jobling et al. |
| 6,133,048 A | 10/2000 | Penfold et al. |
| 6,156,271 A | 12/2000 | May |
| 6,183,972 B1 | 2/2001 | Kuo et al. |
| 6,187,269 B1 | 2/2001 | Lancesseru et al. |
| 6,194,220 B1 | 2/2001 | Malick et al. |
| 6,242,268 B1 | 6/2001 | Wieder et al. |
| 6,261,779 B1 | 7/2001 | Barbera-Guillem et al. |
| 6,274,324 B1 | 8/2001 | Davis et al. |
| 6,294,391 B1 | 9/2001 | Badley et al. |
| 6,352,862 B1 | 3/2002 | Davis et al. |
| 6,362,011 B1 | 3/2002 | Massey et al. |
| 6,368,875 B1 | 4/2002 | Geisberg |
| 6,399,398 B1 | 6/2002 | Cunningham et al. |
| 6,436,651 B1 | 8/2002 | Everhart et al. |
| 6,444,423 B1 | 9/2002 | Meade et al. |
| 6,468,741 B1 | 10/2002 | Massey et al. |
| 6,509,196 B1 | 1/2003 | Brooks et al. |
| 6,524,864 B2 | 2/2003 | Fernandez Decastro |
| 6,582,930 B1 | 6/2003 | Ponomarev et al. |
| 6,585,939 B1 | 7/2003 | Dapprich |
| 6,613,583 B1 | 9/2003 | Richter et al. |
| 6,627,459 B1 | 9/2003 | Tung et al. |
| 6,653,149 B1 | 11/2003 | Tung et al. |
| 6,669,908 B2 | 12/2003 | Weyker et al. |
| RE38,430 E | 2/2004 | Rosenstein |
| 6,893,880 B2 | 5/2005 | Carpenter |
| 6,951,631 B1 | 10/2005 | Catt et al. |
| 7,044,919 B1 | 5/2006 | Catt et al. |
| 7,052,831 B2 | 5/2006 | Fletcher et al. |
| 2002/0042149 A1 | 4/2002 | Butlin et al. |
| 2002/0045273 A1 | 4/2002 | Butlin et al. |
| 2003/0002110 A1 | 1/2003 | Schemmann et al. |
| 2003/0100128 A1 | 5/2003 | Kenjyou et al. |
| 2003/0119202 A1 | 6/2003 | Kaylor et al. |
| 2003/0119204 A1 | 6/2003 | Wei et al. |
| 2003/0124739 A1 | 7/2003 | Song et al. |
| 2004/0029177 A1 | 2/2004 | Nadaoka et al. |
| 2004/0043502 A1 | 3/2004 | Song et al. |
| 2004/0043507 A1 | 3/2004 | Song et al. |
| 2004/0043511 A1 | 3/2004 | Song et al. |
| 2004/0106190 A1 | 6/2004 | Yang et al. |
| 2004/0121334 A1 | 6/2004 | Wei et al. |
| 2004/0121480 A1 | 6/2004 | Wei et al. |
| 2004/0151632 A1 | 8/2004 | Badley et al. |
| 2004/0161859 A1 | 8/2004 | Guo et al. |
| 2004/0197820 A1 | 10/2004 | Wei et al. |
| 2004/0235189 A1 | 11/2004 | Lu |
| 2004/0241700 A1 | 12/2004 | Lamont et al. |
| 2005/0029924 A1 | 2/2005 | Okay et al. |
| 2005/0036148 A1 | 2/2005 | Phelan et al. |
| 2005/0037510 A1 | 2/2005 | Sharrock et al. |
| 2005/0048599 A1 | 3/2005 | Goldberg et al. |
| 2005/0107956 A1 | 5/2005 | Fukunaga et al. |
| 2005/0109951 A1 | 5/2005 | Fish et al. |
| 2005/0112703 A1 | 5/2005 | Song |
| 2005/0112779 A1 | 5/2005 | Wei et al. |
| 2005/0112780 A1 | 5/2005 | Song |
| 2005/0136529 A1 | 6/2005 | Yang et al. |
| 2005/0243321 A1 | 11/2005 | Cohen et al. |
| 2006/0003390 A1 | 1/2006 | Schaffler et al. |
| 2006/0246522 A1 | 11/2006 | Bhullar et al. |

FOREIGN PATENT DOCUMENTS

| | | |
|---|---|---|
| EP | 0253464 A1 | 1/1988 |
| EP | 1219964 A1 | 7/2002 |
| EP | 1 491 892 A1 | 12/2004 |
| WO | WO 97/09620 A | 3/1997 |
| WO | WO 2004 034056 A2 | 4/2004 |
| WO | WO 2004 034056 A3 | 4/2004 |

OTHER PUBLICATIONS

International Search Report and Written Opinion dated Nov. 29, 2006 for Int'l Application No. PCT/US2006/016756.

Search Report and Written Opinion for PCT/US2006/002252, Jun. 29, 2006.

* cited by examiner

DIAGNOSTIC TEST KITS WITH IMPROVED DETECTION ACCURACY

BACKGROUND OF THE INVENTION

Various analytical procedures and devices are commonly employed in flow-through assays to determine the presence and/or concentration of analytes that may be present in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample.

There are several well-known immunoassay methods that use immunoreactants labeled with a detectable component so that the analyte may be detected analytically. For example, "sandwich-type" assay formats typically involve mixing the test sample with detection probes conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semi-quantitative results. Some examples of such sandwich-type assays are described in. by U.S. Pat. No. 4,168,146 to Grubb, et al. and U.S. Pat. No. 4,366,241 to Tom, et al. An alternative technique is the "competitive-type" assay. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al.

Despite the benefits achieved, conventional lateral flow assays still exhibit significant problems. For instance, some assays encounter significant inaccuracies when exposed to relatively high analyte concentrations. When the analyte is present at high concentrations, a substantial portion of the analyte in the test sample may be left in excess and therefore not form complexes with the conjugated probes. Thus, upon reaching the detection zone, the uncomplexed analyte competes with the complexed analyte for binding sites. Because the uncomplexed analyte is not labeled with a probe, it cannot be detected. Consequently, if a significant number of the binding sites become occupied by the uncomplexed analyte, the assay may exhibit a "false negative." This problem is commonly referred to as the "hook effect" or "prozone".

Besides encountering problems at high analyte concentrations, the calibration systems employed by conventional assays are often unreliable. For example, some assays use external calibration systems in which a curve is obtained from standard samples containing a series of known amounts of analyte. The test results may then be compared with the standard curve to extract the presence and/or amount of the analyte in the sample. The external calibration method, however, is often subject to interference from environmental and batch-to-batch variations, and is thus unreliable. Some internal calibration systems have thus been developed to overcome these problems. Unfortunately, many internal calibration techniques are not readily incorporated into lateral flow devices, which involve heterogeneous separation of the analyte using chromatographic methods.

As such, a need still exists for an integrated diagnostic test kit that is capable of accurately determining the presence or quantity of an analyte over a broad range of possible concentrations.

SUMMARY OF THE INVENTION

In accordance with one embodiment of the present invention, a diagnostic test kit for detecting the presence or quantity of a test analyte within a test sample is disclosed. The diagnostic test kit comprises detection probes conjugated with a first specific binding member that is configured to preferentially bind to the test analyte, and calibration probes conjugated with a second specific binding member that is configured to preferentially bind to a calibration analyte. The kit also comprises a lateral flow assay device comprising a porous membrane, the porous membrane defining a detection zone, indicator zone, and calibration zone. A first receptive material is immobilized within the detection zone that is configured to preferentially bind to the test analyte. A second receptive material is immobilized within the indicator zone that is configured to preferentially bind to uncomplexed conjugated detection probes. In addition, a third receptive material is immobilized within the calibration zone that is configured to preferentially bind to the calibration analyte.

In accordance with another embodiment of the present invention, a method for quantitatively or semi-quantitatively detecting a test analyte within a test sample is disclosed. The method comprises i) contacting the test sample with a porous membrane of a lateral flow device, the porous membrane defining a detection zone, an indicator zone located downstream from the detection zone, and a calibration zone; ii) measuring the intensity of a detection signal produced at the detection zone, the intensity of an indicator signal produced at the indicator zone, and the intensity of a calibration signal produced at the calibration zone; iii) normalizing the measured detection and indicator signal intensities with the calibration signal intensity; and iv) comparing the normalized indicator signal intensity to a reference standard, wherein the reference standard represents an intensity or range of intensities of the indicator signal at or near a saturation concentration of the test analyte.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 2 shows exemplary dose response curves in which FIG. 2A illustrates the relationship between measured detection, indicator, and calibration signal intensities versus analyte concentration, and in which

Figure 1:
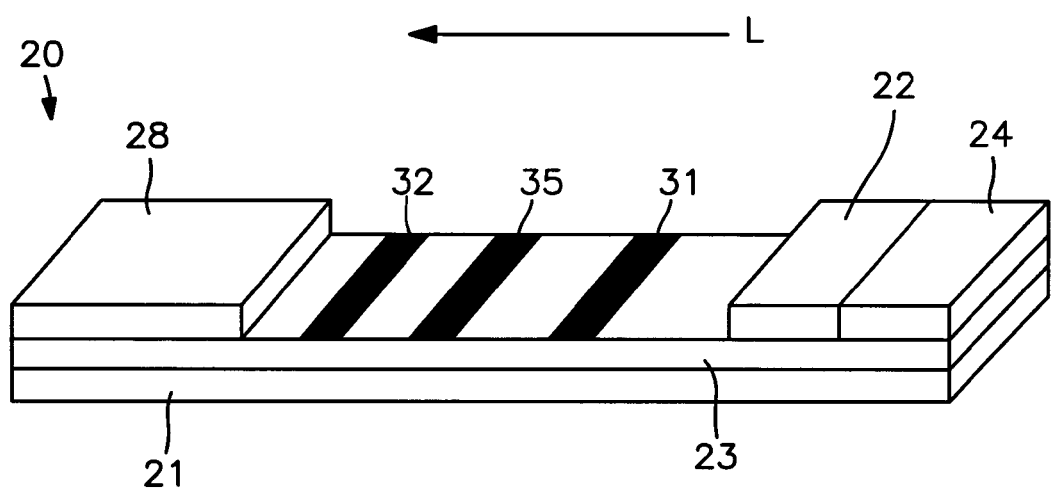
FIG. 1 is a perspective view of one embodiment of a lateral flow assay device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a biological material suspected of containing the analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a diagnostic test kit that provides an integrated system for accurately detecting a test analyte over a broad range of possible concentrations. One feature of the integrated system is that it is capable of indicating whether an analyte is within the "hook effect" region. Based on this indication, a technique may be selected for correlating a measured signal intensity to an analyte concentration or range of concentrations. For example, when it is determined that the test sample falls outside the "hook effect" region, the analyte concentration may be determined using one portion of a dose response curve. On the other hand, when it is determined that the test sample falls within the "hook effect" concentration, the analyte concentration may be determined using another portion of the dose response curve. Alternatively, the sample may simply be diluted for re-performing the assay. Regardless of whether the test sample is within or outside of the "hook effect" concentration, another feature of the integrated detection system of the present invention is that it is internally calibrated to provide a more accurate quantitative or semi-quantitative result to a user.

The test kit employs a lateral flow assay device and a plurality of assay reagents for detecting the test analyte. The assay reagents include detection probes that are capable of producing a detection signal representing the presence or quantity of the test analyte in the test sample. To further enhance detection accuracy, calibration probes are also used that are capable of producing a calibration signal representing the presence or quantity of a calibration analyte. The calibration analyte is normally either foreign to the test sample or present at a constant concentration so that it is easier to distinguish between the test analyte and calibration analyte. Further, it is also normally desired that the calibration analyte exhibit a similar degradation profile (or loss of activity over time) to the test analyte with respect to conditions of pH, temperature, salt concentration, etc. In this manner, the calibration analyte will behave similarly under the same reaction conditions and storage time so that the calibration curve of the calibration analyte will be substantially similar to the calibration curve of the test analyte. If desired, for example, the calibration analyte may be a member of the same protein family as the test analyte. In one embodiment, the test analyte is C-reactive protein ("CRP"), which is a globulin that forms a precipitate with the somatic C-polysaccharide of the *Streptococcus pneumoniae*. CRP belongs to the "pentraxin" family of proteins, which are oligomeric plasma proteins that have a pentagonal cyclic symmetry with five noncovalently bound subunits. There are two common branches of the "pentraxin" family, i.e., "CRP-like" proteins and Serum Amyloid P ("SAP") like proteins. Proteins that bind phosphocholine are considered CRP-like, while proteins that bind carbohydrate moieties are considered SAP-like. Thus, in an embodiment in which CRP is the test analyte, the selected calibration analyte may be a member of the pentraxin family, and even more desirably a pentraxin protein that binds with phosphocholine. Some examples of such phosphocholine-binding pentraxin proteins include, but are not limited to, pentraxin 3 ("PTX3"), neuronal pentraxin 1, and neuronal pentraxin 2. See e.g., *Arteriosclerosis, Thrombosis, and Vascular Biology: Production of the Long Pentraxin PTX3 in Advanced Atherosclerotic Plaques*; Michael S. Rolph, et al.; 2002; 22:e10. However, it is not necessary that the calibration analyte is a member of the same family as the test analyte. In fact, many applications require a lower level of calibration accuracy, and as such, less expensive and more readily available calibration analytes may be employed. In one embodiment, for example, a calibration analyte for CRP may be a protein selected from a non-pentraxin family of proteins (e.g., dimer, trimer, etc.), such as albumin, bovine serum albumin (BSA), β-casein, or hCG, all of which are believed to have a similar degradation profile as CRP.

As stated above, detection and calibration probes are employed in the present invention for detecting the test analyte and calibration analyte, respectively. The calibration probes generally contain the same type of detectable substance as the detection probes. Any substance capable of producing a signal that is detectable visually or by an instrumental device may be used as the detection or calibration probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal. For example, suitable fluorescent molecules may include, but are not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem. et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or nonaqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine] 2-[3-(4-methyl-2,2'-bipyridine-4-yl)propyl]-1,3-dioxolane ruthenium (II); bis(2,2'-bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid] ruthenium (II); tris(2,2'bipyridine)ruthenium (II); (2,2'-bipyridine) [bis-bis(1,2-diphenylphosphino)ethylene] 2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2,2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, luminescent compounds may have a relatively long emission lifetime and a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm(III)), dysprosium (Dy(III)), europium (Eu(III)), and terbium (Tb(III)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N, N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; and U.S. Pat. No. 5,637,509 to Hemmila, et al., which are incorporated herein in their entirety by reference thereto for all purposes.

Detectable substances, such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethyl methacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al. and U.S. Pat. No. 5,252,459 to Tarcha, et al. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns.

It is generally desired to modify the detection and calibration probes in some manner so that they are more readily able to bind to a respective analyte. In such instances, the probes may be modified with certain specific binding members that are adhered thereto to form conjugated probes. Specific binding members generally refer to a member of a specific binding pair, i.e., two different molecules where one of the molecules chemically and/or physically binds to the second molecule. The selection of the specific binding member generally depends on the test analyte of interest and on the corresponding calibration analyte. To ensure independent assay performance, it is normally desired that the detection probes are conjugated with a member of a different specific binding pair than the calibration probes. In this manner, the conjugated calibration probes will preferentially bind with the calibration analyte. The conjugated calibration probes will not, however, generally bind with the test analyte or with a specific binding member for the test analyte. As such, assays may be simultaneously performed for the test analyte and the calibration analyte without fear of substantial cross-reaction, thereby allowing the calibration analyte assay to be used in calibrating the test antigen. Also, similar to the relationship between the calibration analyte and the test analyte, it is normally desired that the specific binding members exhibit a similar degradation profile with respect to conditions of pH, temperature, salt concentration, storage time, etc.

Some examples of suitable immunoreactive specific binding members that may be used in the present invention include, but are not limited to, antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art.

Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The specific binding members may generally be attached to the probes using any of a variety of well-known techniques. For instance, covalent attachment of the specific binding members to the probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the probe may contain a relatively high surface concentration of polar groups. In addition, although probes are often functionalized after synthesis, such as with poly(thiophenol), the probes may be capable of direct covalent linking with a protein without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). The resulting probes may then be contacted with ethanolamine, for instance, to block any remaining activated sites. Overall, this process forms a conjugated probe, where the antibody is covalently attached to the probe. Besides covalent bonding, other attachment techniques, such as physical adsorption, may also be utilized in the present invention.

Regardless of the manner in which they are formed, the detection probes and calibration probes are typically disposed on the assay device prior to application of the test sample. The pre-application of the probes to the assay device provides a variety of benefits. For example, pre-application eliminates the need for a subsequent user to handle and mix the reagents with the test sample or a diluent. This is particularly useful in point-of-care applications where the user is not generally a trained lab technician or medical professional. In some embodiments, for example, the detection and calibration probes are disposed downstream from the point where the test sample is to be applied. In this manner, the test sample is capable of mixing with and optionally re-suspending the probes upon application. Alternatively, the probes may be positioned upstream from the point of application of the test sample. For instance, a diluent may be employed to re-suspend the probes for performing the assay. Similarly, the calibration analyte may also be disposed on the assay device prior to application of the test sample. Although the particular location may vary, it is generally desired that the calibration analyte is applied upstream from the detection probes and calibration probes. In this manner, the calibration analyte is able to readily mix with the test sample before contacting the calibration probes, thereby enhancing binding therebetween.

The calibration analyte may also be mixed with the test sample prior to application to the assay device. As such, the calibration analyte is subjected to substantially the same conditions as the test analyte prior to performance of the assay. This may further optimize calibration accuracy.

Referring now to FIG. 1, one embodiment of a lateral flow assay device 20 that may be employed in the present invention will now be described in more detail. As shown, the device 20 contains a porous membrane 23 optionally supported by a rigid material 21. In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms. One particularly suitable example of a nitrocellulose membrane is "HF 120", which is commercially available from Millipore, Inc.

The size and shape of the porous membrane 23 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 21 carries the porous membrane 23. For example, the support 21 may be positioned directly adjacent to the porous membrane 23 as shown in FIG. 1, or one or more intervening layers may be positioned between the porous membrane 23 and the support 21. Regardless, the support 21 may generally be formed from any material able to carry the porous membrane 23. The support 21 may be formed from a material that is transmissive to light, such as transparent or optically diffuse (e.g., translucent) materials. Also, it is generally desired that the support 21 is liquid-impermeable so that fluid flowing through the membrane 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the porous membrane 23, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known the art, the porous membrane 23 may be cast onto the support 21, wherein the resulting laminate may be die-cut to the desired size and shape. Alternatively, the porous membrane 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate assay device structures are described in U.S. Pat. No. 5,075,077 to Durley, III, et al., which is incorporated herein in its entirety by reference thereto for all purposes.

The device 20 may also contain an absorbent pad 28. The absorbent pad 28 generally receives fluid that has migrated through the entire porous membrane 23. As is well known in the art, the absorbent pad 28 may assist in promoting capillary action and fluid flow through the membrane 23.

To initiate the detection of an analyte within the test sample, a user may directly apply the test sample to a portion of the porous membrane 23 through which it may then travel in the direction illustrated by arrow "L" in FIG. 1. Alternatively, the test sample may first be applied to a sample pad 24 that is in fluid communication with the porous membrane 23. Some suitable materials that may be used to form the sample pad 24 include, but are not limited to, nitrocellulose, cellulose, porous polyethylene pads, and glass fiber filter paper. If desired, the sample pad 24 may also contain one or more assay pretreatment reagents, either diffusively or non-diffusively attached thereto. For example, in one embodiment, the calibration analyte may be disposed on the sample pad 24 so that it contacts the test sample upon application thereto.

In the illustrated embodiment, the test sample travels from the sample pad 24 to a conjugate pad 22 that is placed in communication with one end of the sample pad 24. The conjugate pad 22 is formed from a material through which the test sample is capable of passing. For example, in one embodiment, the conjugate pad 22 is formed from glass fibers. Although only one conjugate pad 22 is shown, it should be understood that multiple conjugate pads may also be used in the present invention. In one particular embodiment of the present invention, the detection and calibration probes (not shown) are applied to the conjugate pad 22. After application, the probes are then dried to inhibit migration therefrom. The conjugate pad 22 provides a matrix for the deposition of the probes so that they are free to migrate when rehydrated. More specifically, when a liquid test sample contacts the probes, they are rehydrated and become re-suspended and/or re-solubilized. Of course, it should be understood that the probes may be applied to various other locations of the assay device 20 as well, such as directly to the membrane 23, so long as they are capable of being rehydrated by the test sample upon contact therewith.

Referring again to FIG. 1, the porous membrane 23 also defines various zones configured to perform the assay. For instance, the porous membrane 23 defines a detection zone 31 that contains a first receptive material. The first receptive material is immobilized on the porous membrane 23 and may be selected from the same materials as the specific binding members described above, including, for instance, antigens; haptens; antibody-binding proteins, such as protein A, protein G, or protein A/G; neutravidin (a deglysolated avidin derivative), avidin (a highly cationic 66,000-dalton glycoprotein), streptavidin (a nonglycosylated 52,800-dalton protein), or captavidin (a nitrated avidin derivative); primary or secondary antibodies, and derivatives or fragments thereof. In some embodiments, the first receptive material is an antibody, such as a monoclonal antibody. The first receptive material may serve as a stationary binding site for complexes formed between the analyte and the conjugated detection probes. Specifically, analytes, such as antibodies, antigens, etc., typically have two or more binding sites (e.g., epitopes). Upon reaching the detection zone 31, one of these binding sites is occupied by the specific binding member of the conjugated probe. However, the free binding site of the analyte may bind to the immobilized first receptive material. Upon being bound to the immobilized receptive material, the complexed probes form a new ternary sandwich complex.

The assay device 20 also contains an indicator zone 35 that is positioned downstream from the detection zone 31 and contains a second receptive material that is immobilized on the porous membrane 23. The second receptive material serves as a stationary binding site for the conjugated detection probes. To accomplish the desired binding within the indicator zone 35, it is generally desired that the second receptive material is capable of differentiating between those detection probes that are complexed with the analyte and those that remain uncomplexed. For example, in one embodiment, the second receptive material includes a molecule that has at least one epitope in common with the analyte, such as analyte molecules, or derivatives or fragments (i.e., analog) thereof, so that it is capable of specifically binding to an antibody conjugate when it is uncomplexed with the analyte. One particularly suitable receptive material for the indicator zone 35 may be C-reactive protein. Alternatively, the second receptive material may include a biological material that is not an analyte molecule or analog thereof, but nevertheless is capable of preferentially binding to uncomplexed conjugated detection probes. In one embodiment, for example, the first receptive material may be a monoclonal antibody, such as anti-CRP $IgG_1$. The detection probes are conjugated with a monoclonal antibody different than the monoclonal antibody of the first receptive material, such as anti-CRP $IgG_2$. In this particular embodiment, the second receptive material may be a secondary antibody, such as Goat anti-human, IgG $F(ab')_2$, which has been adsorbed against $F_c$ fragments and therefore reacts only with the $F_{ab}$ portion of IgG. Thus, when no analyte is present, the secondary antibody is able to bind to the free "$F_{ab}$" binding domain of the anti-CRP $IgG_2$ monoclonal antibody. However, when an antigen is present in the test sample, it first complexes with the "$F_{ab}$" binding domain of the anti-CRP $IgG_2$ monoclonal antibody. The presence of the antigen renders the "$F_{ab}$" binding domain unavailable for subsequent binding with the secondary antibody. In this manner, the secondary antibody within the indicator zone 35 is capable of preferentially binding to uncomplexed detection probes. Still other suitable receptive materials that may be used in the indicator zone 35 are described in more detail in co-pending and co-owned U.S. application Ser. No. 11/119,262 filed on Apr. 29, 2005, which is incorporated herein in its entirety by reference thereto for all purposes.

The assay device 20 also includes a calibration zone 32 that is formed on the porous membrane 23 and positioned downstream from the detection zone 31 and indicator zone 35. Alternatively, however, the calibration zone 32 may also be positioned upstream from the detection zone 31 and/or indicator zone 35. The calibration zone 32 is provided with a third receptive material. The third receptive material may be a member of the specific binding pair used for conjugating the calibration probes. In this manner, the third receptive material preferentially binds to the calibration probes (or complexes thereof). For example, when the calibration analyte is an antigen, the third receptive material may be an antibody. Also, as discussed above, it is normally desired that the first and third receptive materials exhibit a similar degradation profile with respect to conditions of pH, temperature, salt concentration, storage time, etc. Still other suitable receptive materials that may be used in the calibration zone 32 are described in more detail in co-pending and co-owned U.S. application Ser. No. 11/094,498 filed on Mar. 30, 2005, which is incorporated herein in its entirety by reference thereto for all purposes.

The detection zone 31, indicator zone 35, and calibration zone 32 may each provide any number of distinct detection regions so that a user may better determine the concentration of the analyte within the test sample. Each region may contain the same receptive materials, or may contain different receptive materials. For example, the zones may include two or more distinct regions (e.g., lines, dots, etc.). The regions may be disposed in the form of lines in a direction that is substantially perpendicular to the flow of the test sample through the assay device 20. Likewise, in some embodiments, the regions may be disposed in the form of lines in a direction that is substantially parallel to the flow of the test sample through the assay device 20.

Figure 3:
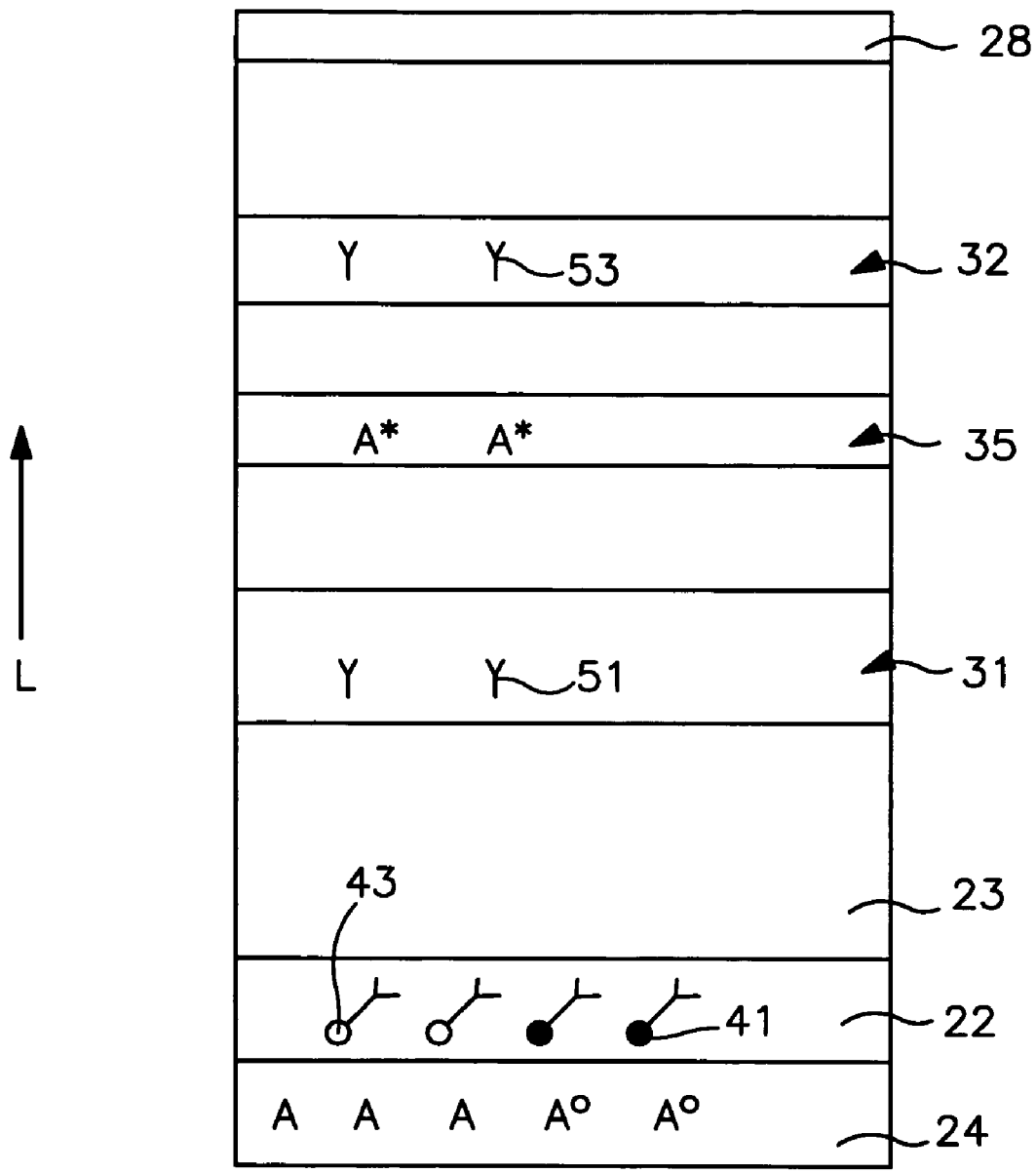
FIG. 3 is a schematic illustration of the mechanism used for one embodiment of the present invention prior to performance of the assay.
Figure 4:
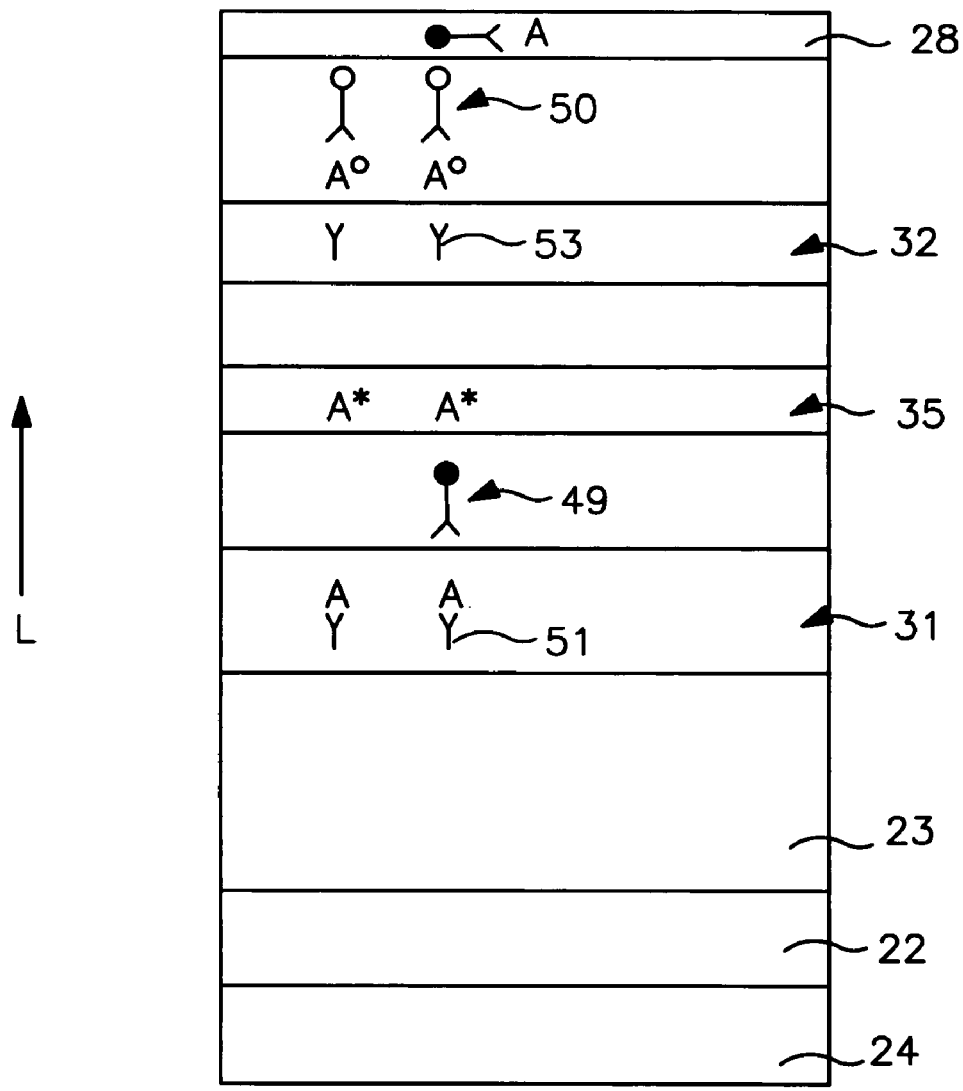
FIG. 4 illustrates the embodiment of FIG. 3 after completion of the assay.

Regardless of their particular configuration of the assay device 20, the detection zone 31, indicator zone 35, and calibration zone 32 function in tandem to improve the analyte detection accuracy. Referring to FIGS. 3-4, one particular embodiment of a method for detecting the presence of an excess concentration of antigen (e.g., CRP) using a sandwich assay format will now be described in more detail. Initially, a calibration antigen $A^0$ (e.g., PTX3) is pre-applied to the sample pad 24, and conjugated detection probes 41 and conjugated calibration probes 43 are pre-applied to the conjugate pad 22. In one embodiment, for example, the detection probes 41 are dyed particles conjugated with an antibody for CRP (e.g., CRP $IgG_1$) and the calibration probes 43 are dyed particles conjugated with an antibody for PTX3 that does not cross-react with other pentraxin family members (e.g., rat anti-body PTX3 (clone MNB4)). To initiate the assay, a test sample containing the test antigen A is applied to the sample pad 24 where it mixes with the calibration antigen $A^0$. The test antigen A and calibration antigen $A^0$ travel in a direction "L" to the conjugate pad 22, where they mix with the conjugated detection probes 41 and calibration probes 43. The test antigen A binds with the detection probes 41 to form analyte/probe complexes 49, and the calibration antigen $A^0$ binds with the calibration probes 43 to form analyte/probe complexes 50. Some of the antigen A remains free due to the limited availability of the conjugated detection probes 41.

As shown in FIG. 4, the free antigen A and complexes 49 and 50 then travel to the detection zone 31, within which is immobilized a first antibody 51. For example, the first antibody may be an antibody for CRP that is different than the antibody of the conjugated detection probes (e.g., anti-CRP $IgG_2$) or an antibody for CRP that is identical to the antibody conjugated to the detection probes. The free antigen A and the complexes 49 compete for binding sites on the immobilized antibody 51. Any remaining antigen A and complexes 49 travel to the indicator zone 35, within which is immobilized a molecule A* that is identical in nature to the antigen A. However, because the antigen A and complexes 49 do not possess a site for binding to the molecule A*, they generally pass through the indicator zone 35 until they reach the absorbent pad 28. Likewise, the complexes 50 formed by the calibration probes and the calibration analyte travel to the calibration zone 32, within which is immobilized a second antibody 53. For example, the second antibody may be an antibody for PTX3 that is the same or different than the antibody of the conjugated calibration probes (e.g., a different clone of rat anti-body PTX3). The complexes 50 bind to the available binding sites on the second antibody 53. The intensity of the signals produced by any detection probes 41 captured at the detection zone 31 and the indicator zone 35 may then be measured. In addition, the intensity of the signal produced by the calibration probes 43 at the calibration zone 32 may also be measured, which generally remains constant for any analyte concentration.

If desired, an optical reader may be used in some embodiments to measure the intensity of the probes. The actual configuration and structure of the optical reader may generally vary as is readily understood by those skilled in the art. For example, optical detection techniques that may be utilized include, but are not limited to, luminescence (e.g., fluorescence, phosphorescence, etc.), absorbance (e.g., fluorescent or non-fluorescent), diffraction, etc. One suitable reflectance spectrophotometer is described, for instance, in U.S. Patent App. Pub. No. 2003/0119202 to Kaylor, et al., which is incorporated herein in its entirety by reference thereto for all purposes. In another embodiment, a reflectance-mode spectrofluorometer may be used to detect the presence of probes that exhibit fluorescence. Suitable spectrofluorometers and related detection techniques are described, for instance, in U.S. Patent App. Pub. No. 2004/0043502 to Song, et al., which is incorporated herein in its entirety by reference thereto for all purposes. Likewise, a transmission-mode detection system may also be used to detect the presence of detection probes.

Typically, the optical reader contains an illumination source that is capable of emitting electromagnetic radiation and a detector that is capable of registering a signal (e.g., transmitted or reflected light, emitted fluorescence or phosphorescence, etc.). The illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some cases, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. One commercially available example of a suitable UV LED excitation diode suitable for use in the present invention is Model NSHU55OE (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

In some cases, the illumination source may provide diffuse illumination to the assay device. For example, an array of multiple point light sources (e.g., LEDs) may simply be employed to provide relatively diffuse illumination. Another particularly desired illumination source that is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to emit light.

The detector may generally be any device known in the art that is capable of sensing a signal. For instance, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into a system for use with a membrane-based device. If silicon photodiodes are used, then the wavelength range of the emitted signal may be within their range of sensitivity, which is 400 to 1100 nanometers.

Generally speaking, qualitative, quantitative, or semi-quantitative determination of the presence or concentration of an analyte may be achieved in accordance with the present invention. For example, as stated above, the amount of the analyte may be quantitatively or semi-quantitatively determined by using the intensities of the signals produced by probes captured at the detection zone 31, the indicator zone 35, and the calibration zone 32. The ability to utilize different signal intensities to determine analyte concentration is illustrated graphically in FIGS. 2A and 2B. It should be understood that the signal intensities do not necessarily have to follow the illustrated relationship, and that this relationship is given for exemplary purposes only.

Figure 2A:
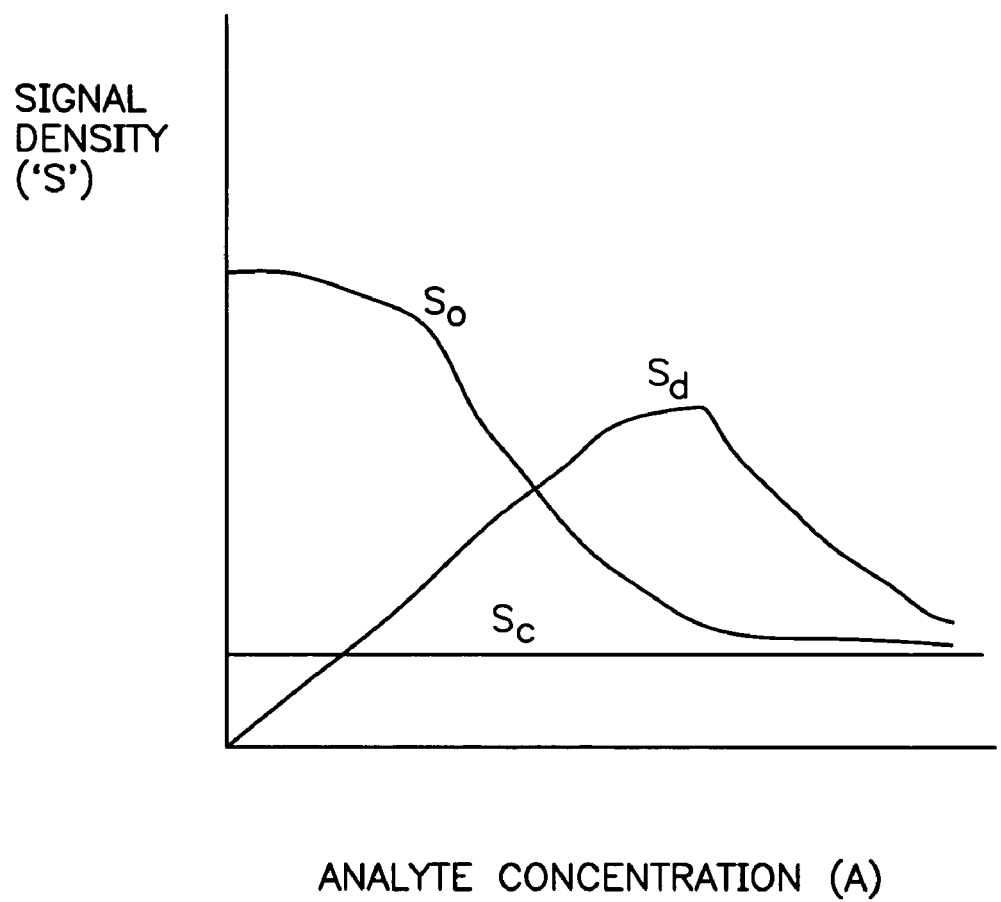

In this regard, FIG. 2A shows the relationship of the signal intensity of the detection probes and calibration probes of FIGS. 3 and 4 for the indicator zone 35, the detection zone 31, and the calibration zone 32. As shown, when no antigen A is present in the test sample, all of the detection probes 41 bind to the antigen A* within the indicator zone 35 and produce an indicator signal intensity ("$S_o$") that is at a maximum value. The detection zone 31 produces no signal. As its concentration increases, the antigen A begins to form complexes 49 with the conjugated detection probes 41. The complexes 49 possess an epitope capable of binding with the antibody 51 at the detection zone 31. This causes a decrease in the indicator signal intensity "$S_o$", and also causes the production of a detection signal intensity "$S_d$" at the detection zone 31. The intensity of the indicator signal "$S_o$" continues to decrease and the intensity of the detection signal "$S_d$" continues to increase until the concentration of the antigen A exceeds the amount of available conjugated detection probes 41. This is known as the "saturation concentration" of the analyte. At the saturation concentration, the free analyte A and complexes 49 begin to compete for binding sites at the detection zone 31. Accordingly, the intensity of the detection signal "$S_d$" reaches its maximum value. This value is generally known because the amount of detection probes 41 is selected to correspond to the amount of the available antibody 51 at the detection zone 31. As the antigen concentration increases further, the detection signal intensity "$S_d$" begins to decrease due to the escalating presence of free, unlabeled antigen A within the detection zone 31. Moreover, at or near the analyte saturation concentration, no indicator signal intensity will theoretically be detected as all of the detection probes 41 will complex with the analyte A, and subsequently bind to the antibody 51 within the detection zone 31. In practice, however, a small number of detection probes 41 may bind to the antigen A* within the indicator zone 35 such that a relatively low indicator signal intensity "$S_o$" is still produced.

Because a predetermined and known amount of calibration analyte and calibration probes 43 are employed, the signal intensity "$S_c$" of the calibration zone 32 remains substantially constant regardless of the analyte concentration. Consequently, the signal intensity "$S_c$" may be used to calibrate the intensity of the detection signal "$S_d$" and/or the intensity of the indicator signal "$S_0$" to improve the accuracy of the results. For example, the ratio of $S_d$ to $S_c$ (i.e., "normalized detection signal intensity", ($I_d$) may be calculated for a plurality of known analyte concentrations to develop a normalized dose response curve. Similarly, the ratio of $S_o$ to $S_c$ (i.e., "normalized indicator signal intensity", $I_o$) may also be calculated for a plurality of known analyte concentrations to develop a normalized dose response curve. Of course, it should be understood that any other mathematical relationship between "$S_c$" and "$S_o$" and "$S_d$" may also be employed to calculate the normalized signal intensities.

Figure 2B:
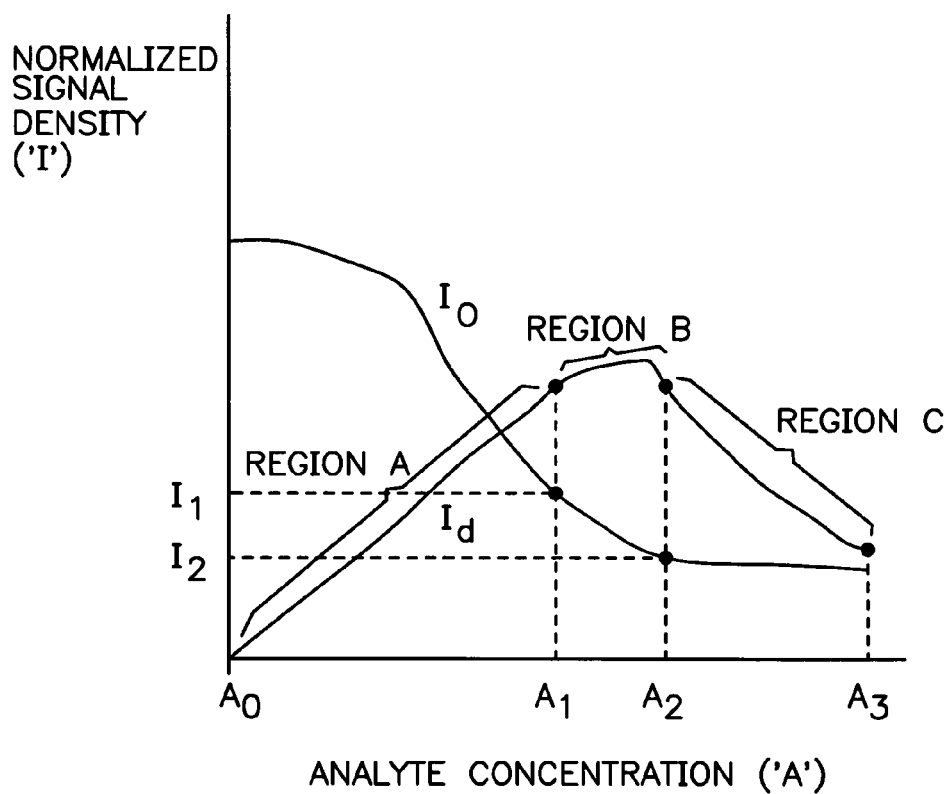
FIG. 2B illustrates the relationship between normalized detection and indicator signal intensities versus analyte concentration.

One example of a suitable normalized dose response curve is illustrated in FIG. 2B. Various regions of the normalized dose response curve may be selectively employed to convert a measured and normalized detection signal intensity "$I_d$" (e.g., $S_d/S_c$) to analyte concentration. For example, "Region A" of the curve is defined between analyte concentrations "$A_o$" and "$A_1$." In this region, detection signal intensity bears an almost linear relationship with analyte concentration. Thus, "Region A" of FIG. 2B may be used to accurately convert the measured and normalized detection signal intensity "$I_d$" to an actual analyte concentration. Likewise, "Region C" defines of the curve is defined between analyte concentrations "$A_2$" and $A_3$." Again, in this region, detection signal intensity bears an almost linear relationship with analyte concentration. Thus, "Region C" of FIG. 2B may also be used to accurately convert the measured and normalized detection signal intensity "$I_d$" to an actual analyte concentration. "Region B" of the detection curve, which is defined between analyte concentrations "$A_1$" and "$A_2$" is relatively constant, and as such, it is sometimes difficult to obtain an accurate correlation to analyte concentration. Thus, if quantitative results are desired, the user may dilute a subsequent test sample and then re-perform the assay. Alternatively, the normalized indicator signal intensity "$I_o$" (e.g., $S_o/S_c$) may be used alone or in conjunction with the normalized detection signal intensity "$I_d$" to provide a quantitative result. If only semi-quantitative results are desired, the analyte concentration may simply be said to fall within between the range of analyte concentrations "$A_1$" and $A_2$."

To determine which region of the normalized dose response curve of FIG. 2B is most suited for a particular test sample, it is generally desired to first determine whether the analyte concentration is within the "hook effect" region. In this regard, a measured and normalized indicator signal intensity "$I_o$" may be compared to a reference standard that is predetermined for a known saturation concentration of the analyte. The "reference standard" may be a single intensity value or it may encompass a range of values that are believed to correspond to the saturation concentration within a certain margin of error. The upper and lower limit of the range of values may be selected based on the extent the normalized indicator signal intensity varies over multiple test runs for the same known analyte saturation concentration. For example, in FIG. 2B, the reference standard may be defined between normalized intensity values "$I_1$" and "$I_2$", which correspond to analyte concentrations "$A_1$" and "$A_2$", respectively. A measured and normalized signal intensity "$I_o$" that is greater than the reference standard (e.g., greater than the upper limit "$I_1$") serves as an indicator that the analyte concentration is outside of the "hook effect" region, while a measured, normalized signal intensity "$I_o$" that is the same or less than the reference standard (e.g., less than the upper limit "$I_1$") serves as an indicator that the analyte concentration is within the "hook effect" region.

Figure 5:
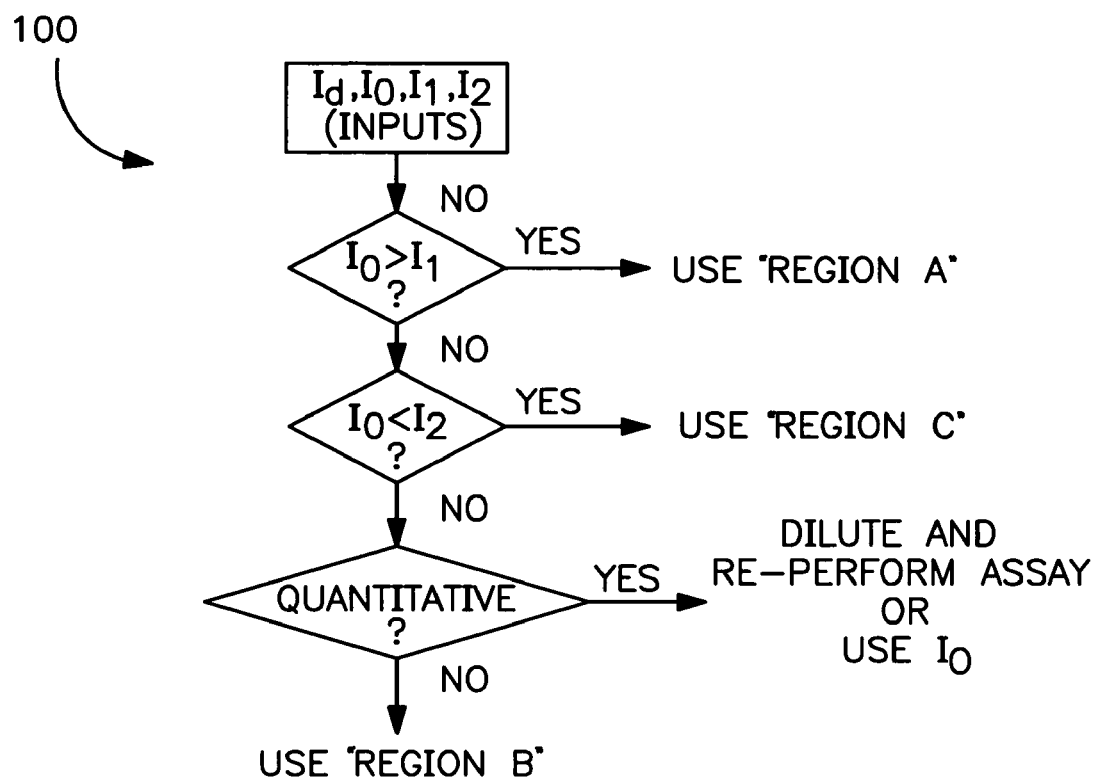
FIG. 5 illustrates one embodiment of a method for determining whether an analyte concentration is within the "hook effect" region, and for semi-quantitatively or quantitatively determining the analyte concentration.

Referring to FIG. 5, for instance, one embodiment of a method 100 is shown for determining whether the analyte concentration is within the "hook effect" region. Several variables are used as inputs in the method 100, including the measured, normalized detection signal intensity "$I_d$"; the measured, normalized indicator signal intensity "$I_o$"; and the upper limit $I_1$ and lower limit $I_2$ of the reference standard. The first step of the method 100 is to determine whether the measured, normalized signal intensity "$I_o$" is greater than the upper limit "$I_1$". If so, the analyte concentration is outside the "hook effect" region, and "Region A" of the normalized dose response curve may be used to convert the measured detection signal intensity "$I_d$" to an analyte concentration. If the measured, normalized signal intensity "$I_o$" is less than the upper limit "$I_1$", the next step of the method 100 is to determine whether the analyte concentration is at or near the saturation concentration, or if it is well above the saturation concentration. Thus, the method 100 determines whether the measured, normalized signal intensity "$I_o$" is less than the lower limit "$I_2$", and if so, "Region C" of the normalized dose response curve may be used to convert the measured, normalized detection signal intensity "$I_d$" to an analyte concentration. If the measured, normalized signal intensity "$I_o$" is greater than the lower limit "$I_2$" but less than the upper limit "$I_1$" (i.e., the same as the reference standard), the final step of the method 100 is to determine whether semi-quantitative or quantitative results are desired. If quantitative results are desired, the method 100 instructs the user to dilute a subsequent test sample and then re-perform the assay. Alternatively, the measured, normalized indicator signal intensity "$I_o$" may also be used alone, or in conjunction with the normalized detection signal intensity "$I_d$" to provide quantitative results. For example, as shown in FIG. 2B, the indicator curve is relatively linear within "Region B" of the detection signal curve. Thus, within this region, the indicator curve may provide accurate detection results. Moreover, if only semi-quantitative results are desired, the method 100 simply indicates that the analyte concentration falls within the range of analyte concentrations "$A_1$" and "$A_2$" shown in FIG. 2.

Correlation methods, such as described above, may be performed automatically and/or manually. For example, a microprocessor may optionally be employed to automatically select the desired correlation technique and to convert the measurement from the detector to a result that quantitatively or semi-quantitatively indicates the concentration of the analyte. The microprocessor may include memory capability to allow the user to recall the last several results. Those skilled in the art will appreciate that any suitable computer-readable memory devices, such as RAM, ROM, EPROM, EEPROM, flash memory cards, digital video disks, Bernoulli cartridges, and so forth, may be used. If desired, the results may be conveyed to a user using a liquid crystal (LCD) or LED display.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diagnostic test kit for detecting the presence or quantity of a test analyte within a test sample, the diagnostic test kit comprising:
   detection probes conjugated with a first specific binding member that is configured to preferentially bind to the test analyte;
   calibration probes conjugated with a second specific binding member that is configured to preferentially bind to a calibration analyte; and
   a lateral flow assay device on which the detection probes and calibration probes are disposed, the lateral flow assay device comprising a porous membrane, the porous membrane defining:
   a detection zone in which is immobilized a first receptive material, the first receptive material being configured to preferentially bind to the test analyte;
   an indicator zone in which is immobilized a second receptive material, the second receptive material being configured to preferentially bind to uncomplexed conjugated detection probes; and
   a calibration zone in which is immobilized a third receptive material, the third receptive material being configured to preferentially bind to the calibration analyte;
   wherein the lateral flow device further comprising a conjugate pad in fluid communication with the porous membrane and a sample pad that is positioned upstream from the conjugate pad, wherein the detection probes and calibration probes are disposed on the conjugate pad and wherein the calibration analyte is disposed on the sample pad.

2. The diagnostic test kit of claim 1, wherein the detection probes comprise a luminescent compound or visual label.

3. The diagnostic test kit of claim 1, wherein the test analyte is a pentraxin protein.

4. The diagnostic test kit of claim 3, wherein the test analyte is C-reactive protein.

5. The diagnostic test kit of claim 1, wherein the calibration analyte and the test analyte are members of the same protein family.

6. The diagnostic test kit of claim 1, wherein the calibration analyte and the test analyte are members of different protein families.

7. The diagnostic test kit of claim 1, wherein the first and second specific binding members are selected from the group consisting of antibodies, antigens, haptens, protein A, protein G, protein A/G, neutravidin, avidin, streptavidin, captavidin, and analogs thereof.

8. The diagnostic test kit of claim 1, wherein the first, second, and third receptive materials are selected from the group consisting of antibodies, antigens, haptens, protein A, protein G, protein A/G, neutravidin, avidin, streptavidin, captavidin, and analogs thereof.

9. The diagnostic test kit of claim 1, wherein the second receptive material has at least one epitope in common with the test analyte.

10. The diagnostic test kit of claim 9, wherein the second receptive material includes an antigen or an analog thereof.

11. The diagnostic test kit of claim 1, wherein the first receptive material includes an antibody or an analog thereof.

12. The diagnostic test kit of claim 1, wherein the detection zone is located upstream from the indicator zone.

13. The diagnostic test kit of claim 1, wherein the calibration zone is located downstream from the detection zone.

14. The diagnostic test kit of claim 1, wherein the calibration zone is located upstream from the detection zone.

15. The diagnostic test kit of claim 1, wherein the concentration of the analyte is determined by reference to an indicator signal produced by the indicator zone and a detection signal produced by the detection zone, one or both of which are calibrated by a calibration signal produced by the calibration zone.

16. The diagnostic test kit of claim 15, wherein the intensity of the indicator signal is indicative of whether the concentration of the analyte within the test sample is within the hook effect region.

17. The diagnostic test kit of claim 1, wherein the first specific binding member, the second specific binding member, the first receptive material, and the second receptive material are immunoreactive binding members.

* * * * *